(12) United States Patent
Siamon

(10) Patent No.: US 6,506,392 B2
(45) Date of Patent: *Jan. 14, 2003

(54) THERAPUTIC TOPICAL SOLUTION FOR SKIN AND ASSOCIATED METHODS OF USE

(76) Inventor: Al Siamon, 2585 Lara La., Oceana, CA (US) 93445

( * ) Notice: Subject to any disclaimer, the term of this patent is extended or adjusted under 35 U.S.C. 154(b) by 0 days.

This patent is subject to a terminal disclaimer.

(21) Appl. No.: 09/771,443

(22) Filed: Jan. 26, 2001

(65) Prior Publication Data

US 2002/0031555 A1 Mar. 14, 2002

Related U.S. Application Data

(63) Continuation-in-part of application No. 09/657,995, filed on Sep. 8, 2000, now Pat. No. 6,432,425.

(51) Int. Cl.[7] .............................. A61K 6/00; A61K 7/00; A61K 33/42; A01N 59/26; A01N 59/06
(52) U.S. Cl. .................... 424/401; 424/606; 424/686; 424/717
(58) Field of Search ................ 424/401, 47, 606, 424/686, 717; 514/769

(56) References Cited

U.S. PATENT DOCUMENTS

| | | | |
|---|---|---|---|
| 4,115,307 A | 9/1978 | McGilvery | |
| 4,307,089 A * | 12/1981 | Melloh et al. | 424/245 |
| 4,504,995 A | 3/1985 | Zippwald, Sr. | |
| 4,592,892 A * | 6/1986 | Ueno et al. | 422/28 |
| 4,740,366 A | 4/1988 | Winston et al. | |
| 4,828,621 A | 5/1989 | Siamon | |
| 4,851,212 A | 7/1989 | Winston et al. | |
| 5,434,182 A * | 7/1995 | Isaacs et al. | 514/546 |
| 5,552,078 A | 9/1996 | Carr et al. | |
| 5,635,462 A | 6/1997 | Fendler et al. | |
| 5,861,430 A | 1/1999 | Markonius | |
| 5,928,671 A | 7/1999 | Domenico | |
| 6,022,547 A * | 2/2000 | Herb et al. | 424/401 |
| 6,046,160 A | 4/2000 | Obi-Talbot | |
| 6,184,198 B1 * | 2/2001 | Siamon | 510/510 |
| 6,217,887 B1 * | 4/2001 | Beerse et al. | 424/401 |
| 6,225,279 B1 * | 5/2001 | Siamon | 510/510 |

* cited by examiner

Primary Examiner—Dameron L. Jones
Assistant Examiner—Lauren Q. Wells
(74) Attorney, Agent, or Firm—Greenberg Traurig, LLP

(57) ABSTRACT

A formulation consisting of sodium bicarbonate, sodium carbonate and trisodium phosphate in aqueous solution is applied topically to treat an array of skin and tissue problems. The solution offers antibacterial, antiseptic, antifungal, and healing properties to skin scratches, cuts, sores, and fungal infected nails. In addition, the solution dries as a thin film to the applied surfaces, continuously providing antibacterial, anti-fungal and antiseptic activity beneath the protective film long after it has been applied.

26 Claims, No Drawings

THERAPUTIC TOPICAL SOLUTION FOR SKIN AND ASSOCIATED METHODS OF USE

This is a continuation-in-part of application Ser. No. 09/657,995 filed on Sep. 8, 2000 now U.S. Pat. No. 6,432,425 currently pending.

BACKGROUND

1. Field of the Invention

The present disclosure relates to an antiseptic and antibacterial (generally antimicrobial) solution for use on human and animal tissue, and uses thereof.

2. Description of Related Art

The formulation of therapeutic antibacterial and antiseptic solutions, having the ability to kill and/or reduce bacteria, fungus, and other microorganisms while healing wounds or infections, is of significant importance. To this effect, much research in the fields of antibacterial, anti-fungal, and antiseptic agents has been performed and has resulted in a plethora of solutions having a wide variety of formulations. However, while many of these complex compositions provide acceptable antibacterial, antiseptic, anti-fungal, and healing properties, these acceptable properties are often not employed together in one solution, despite the many exotic, expensive components employed. Furthermore, as these compositions do not typically remain on the skin, their antibacterial and anti-fungal properties are short-lived. Finally, many of these products have components that may be harmful to a user if used internally or ingested.

Therefore it would be advantageous to have a therapeutic topical solution capable of having antiseptic and/or healing properties, while encompassing only a few readily available components. In addition, it would be advantageous for the solution to be non-toxic and not cause harm if accidentally used internally or ingested.

SUMMARY

In accordance with the present disclosure, a solution (liquid) that provides the above-mentioned advantages and its methods of use are provided. The present solution consists essentially of a mixture of sodium bicarbonate ($NaHCO_3$, CAS RN 144-55-8), sodium carbonate $Na_2CO_3$, CAS RN 497-19-8) and trisodium phosphate $Na_3PO_4$, CAS RN 10101-89-0) formulated as an aqueous solution of those components, in various concentrations. The mixture of sodium bicarbonate, sodium carbonate, and trisodium phosphate is present in the concentrations listed below, having a particular molar ratio.

In some embodiments, the solution (which is the above-described mixture dissolved in water) is applied topically to cuts, sores, infections and skin irritations. The solution aids in encapsulating bacteria and microorganisms, and prevents their growth. The solution dries and forms a thin film or coating over the surface of the tissue and thus continues to function long after it has been applied. The present solution has also been effective when used to kill fungus on fingernails and toenails and as a treatment for acne related infections.

In some embodiments, the solution is applied to sores, scratches and skin irritations (including psoriasis) to aid in the healing process. Furthermore, the solution when dry forms a thin film or protective barrier over the affected area and continues to protect the wound from contamination for an extended period of time after it has been applied.

In some embodiments, the solution is applied to acne. The solution helps in healing acne by forming a protective barrier over the infected skin follicle which blocks microorganisms from entering, thus eliminating the infection and scarring that might follow.

In some embodiments, the solution is applied to scars, burns, and rashes, wrinkles and "stress lines". "Stress lines" may be described as wrinkles found in and around areas of the mouth, eyes, forehead and the like. As mentioned previously, the solution dries and forms a thin film or coating over the area onto which the solution has been applied. Application of the solution onto skin has been found to be therapeutically effective in reducing the aforementioned scars, rashes wrinkles and "stress lines", respectively.

In another embodiment, the solution is utilized as a topical solution that is part of a regimen for the promotion and/or maintenance of healthy, smooth skin. The solution disclosed herein may be applied to desired, non-damaged, areas of the skin to help maintain the skin in a normal and healthy state.

DETAILED DESCRIPTION

The following is a detailed description of illustrative embodiments. As these embodiments are described, various modifications or adaptations of the methods and or specific structures described may become apparent to those skilled in the art. All such modifications, adaptations or variations that rely upon the teachings of the present disclosure, and through which these teachings have advanced the art, are considered to be within the spirit and scope of the present invention. Hence, these descriptions are not to be considered in a limiting sense, as it is understood that the present invention is in no way limited to the embodiments illustrated.

The present disclosure provides a method of use for a solution for human and animal tissue. For example, the solution is useful for preventing the growth of bacteria on human and animal tissue, including the skin. The solution has proven efficacy in encapsulating bacteria and viruses. Typical poisons act to kill off susceptible populations of bacteria, fungi and the like. A problem with this approach is that there are, typically, members of the bacterial or fungal populations that are naturally "immune" to the poison employed. Therefore, these few surviving bacteria or fungi, for example, propagate and result in a "new" population that is resistant to the aforementioned poison, leading to the search for other types of poisons. The solutions of the present invention encapsulates, with equal efficacy, a population of bacteria or fungi and therefore does not serve as a "selective pressure" on the population, and does not promote the establishment of a population that is now resistant to this preventative method of propagation.

In addition, the solution helps in healing sores, cuts, and skin irritations. It also aids in removing wrinkles, age spots, treating fungus on nails, eczema and in treating psoriasis, a chronic skin inflammation. Furthermore, the solution has also been found to be effective in the promotion of healing and/or reducing irritation of skin that is or has been subjected to trauma or insult, such as, but not limited to, rashes, burns and other injuries. It is also noted that application of the solution also reduces feelings of pain associated with cuts and burns to the skin, by means of a film created when the solution dries. This film does not allow air to irritate the exposed nerves and blood vessels, thus soothing the associated pain.

The solution is also effective in reducing scars and scarring, as well as reducing the signs of aging skin, including wrinkles, for example. By application of the solution on skin, the body's own fluids, stored in the deeper layers of skin tissue, are drawn towards the surface, replenishing the fluids which have been depleted by the ongoing aging process and environmental exposure. In addition, when applied to skin regularly, the solution helps to maintain skin in a healthy, smooth state. The solution also provides a thin protective coating or film to skin surfaces. This protective coating remains on the skin and continues to prevent the growth of microorganisms, bacteria, and fungus, beneath the protective film, long after it has been applied.

For a description pertinent to the solution itself, see commonly invented application Ser. No. 09/098,042 "A Cleaning Solution and Method" filed Jun. 16, 1998 and the corresponding International application Ser. No. PCT/99/1274 filed Jun. 7, 1999, published December, 1999, both incorporated by reference herein in their entirety.

Advantageously, solutions in accordance with the present disclosure are formulated using a mixture of three well-known, readily available substances, sodium bicarbonate ($NaHCO_3$, CAS RN 144-55-8), sodium carbonate ($Na_2CO_3$, CAS RN 497-19-8) and trisodium phosphate ($Na_3PO_4$, CAS RN 10101-89-0). Each of these substances is essentially non-toxic and otherwise safe. Thus sodium bicarbonate is commonly known as baking soda and is often used as an additive in the preparation of foods as well as a cleaning agent. Sodium carbonate, commonly known as washing soda or sal soda, is a well-known cleaning additive or enhancer that also has uses, when in solution, as a skin cleanser for eczema. Finally, trisodium phosphate is well known as a water-softening agent as an ingredient in many common detergent formulations.

The therapeutic antiseptic solution encompassed in certain embodiments is believed to gain its advantageous properties by employing a specific molar ratio of the above mentioned components. This specific molar ratio is then formulated in aqueous solutions of varying concentrations. Thus embodiments are aqueous solutions having various concentrations of a mixture of sodium bicarbonate (hereafter SB), sodium carbonate (hereafter SC) and trisodium phosphate (hereafter TSP) having a molar ratio of approximately 1:2.6:1.6. That is, for every mole of SB, 2.6 moles of SC and 1.6 moles of TSP are used to prepare the solutions.

It is further contemplated that alternative compounds, in similar, approximate molar ratios to those disclosed, may be utilized. Such exemplary compounds include, but are not limited to, potassium bicarbonate, potassium carbonate and tripotassium phosphate, for example. It is considered to be within the scope of the present invention that other alkali metals of the group of IA elements of the periodic table, may be substituted for the alkali metal portion of the compositions (i.e. sodium, for example) disclosed herein.

Additionally, various mixtures or combinations of these alternate compounds are contemplated as being within the scope of the present invention. Such exemplary mixtures may be a solution comprising sodium bicarbonate, potassium carbonate and trisodium phosphate in approximately a 1:2.6:1.6 molar ratio. Similarly, a solution containing potassium bicarbonate, potassium carbonate and trisodium phosphate in approximately a 1:2.6:1.6 molar ratio is also contemplated. It is to be understood that the present invention is not to be limited to the examples mentioned above and that other combinations of these, as well as other alkali carbonate, alkali bicarbonate and tri-alkali phosphate compounds are possible, as known to one skilled in the art.

In a typical nominally "full-strength" formulation, an amount of solution having a first concentration is prepared by combining approximately 910 grams of SB, approximately 1,930 grams of SC and approximately 2,270 grams of TSP in approximately 208 liters of water; the water used is, e.g., deionized water, softened water or water processed through a reverse osmosis (RO) system. Such a typical "full-strength" formulation of the first concentration is thus approximately 2.46 percent (%) solids or active ingredients. It will be understood that the quantity of "full-strength" solution described above is illustrative only and that other quantities having the same molar ratio and percent solids concentration can be readily prepared by one of ordinary skill in the art, for example 100 liters of the "full-strength" solution rather than 208 liters. In addition, it will be understood that while the specific molar ratio of the above components described has been found to be most effective for certain uses, other molar ratios are also effective for other uses. It has also been found that other solids concentrations of the "full-strength" formulation described above are also effective, for example, concentrations as high as approximately 2.7% or as low as approximately 2.2% are also found to be effective specifically as an antiseptic solution, as well as therapeutic for skin.

While "full-strength" formulations are useful as solutions, other formulations having concentrations less than that of the "full-strength" formulation are also found to be effective antibacterial, antiseptic and therapeutic agents. Thus a formulation having a second concentration is prepared by diluting a "full-strength" solution of the first concentration by approximately one-half. Hence, this "half-strength" formulation has a concentration that is 50% of the first concentration; as a result, such a typical formulation is approximately 1.23% solids.

For example, therapeutic solutions that may be utilized for the treatment of chronic skin inflammations, such as psoriasis for example, may be tailored to particular individuals. When utilizing the solution as a treatment for psoriasis, a stronger solution, comprising approximately 4.92% solids or active ingredients, is recommended for topical application. However, in some particular circumstances, some solutions may be deemed too strong for a particular user and elicit an adverse reaction. It is also noted that the therapeutic solutions do not harm the healthy skin surrounding the skin irritations or inflammations.

As an example, in cases where the psoriasis sufferer has or is utilizing other treatments, such as cortisone or predisone, whereby their skin may have become sensitive to the application of the strong (about 4.92%) solution, a milder, diluted form of the solution may be utilized. In such a case, the "full strength" 100% solution (approximately 2.46% solids) or the "half-strength" solution (approximately 1.23% solids), as previously detailed, may be utilized, as judged by testing the various concentrations onto the particular skin area to be treated. Even weaker solutions may be used, having less than 1.23% solids.

A further understanding of the present invention will be afforded by a consideration of the following non-limiting examples. In these examples, the "full strength" 100% solution was utilized. These examples are illustrative of the principals of the present invention and are not intended to limit the scope of the invention to the exemplary uses and formulations.

EXAMPLE 1

This example demonstrates the effect of the formulations and solutions on subjects suffering from the skin disorder, psoriasis. The formulations and solutions of the present invention are applied topically to skin exhibiting psoriasis.

Three subjects, two male and one female, suffering from psoriasis, applied the solution to areas on their bodies and rubbed in the solution with their fingertips several times per day or as needed. Areas of application included knees and elbows.

Following topical application of the solution, itching was immediately eliminated and the appearance of the psoriatic lesions were noticeably improved. Improvements in the appearance of the "scaly" psoriasis effected skin were noticed in as little as six hours. Over extended periods of application of the solution, the continuous buildup of "scaly skin" associated with psoriasis were reduced as a result of the application of the solutions disclosed herein.

It is important to note that some of the subjects had suffered from psoriasis for an extended period of time and had tried a variety of treatments. One subject had previously utilized various tars, cortisones, temovate and methotrexate treatments. Additionally, this subject had also subjected the psoriasis effected areas of the skin to ultraviolet radiation provided by a PUVA ultraviolet box, all without success.

After beginning to utilize the solution disclosed herein, the psoriasis was well on its way to clearing up and significant improvement of the skin's condition was noted. Advantageously, the effectiveness of the solution on the psoriasis was very rapid and obvious, a unique experience for the users.

EXAMPLE 2

This example demonstrates the effect of the formulations and solutions on scar tissue. The formulations and solutions of the present invention are applied topically to skin exhibiting scar tissue in order to reduce the roughness apparent in traumatized skin. As in Example 1, the solution is applied to the skin and then rubbed in utilizing the fingertips.

In this example, a female subject had experienced major head trauma which had left a scar across the forehead. The subject has been applying various products over the past four years in order to reduce the "roughness" associated with the scar tissue which had formed as a result of the head injury.

Upon topical application of the solution as needed, the appearance of the scar tissue was notably improved. The scar tissue became extremely smooth, whereas it had been very rough prior to the application of the solution. This "smoothening effect" was manifested in the space of one hour.

EXAMPLE 3

This example demonstrates the effect of the formulations and solutions upon rashes as well as wrinkles. In this example three subjects, one male and two female, were suffering from various skin-disorders.

The male subject had been involved in an automobile accident. As a result of this accident, surgery had been performed on his right knee. Afterward and since, this subject has suffered from a rash that is located around the right knee as well as on the right upper hip and thigh. This rash is bumpy, reddish in color and scaly, itching and irritating this subject.

The male subject applied the solution to the afflicted areas several times per day, each time rubbing the solution into the skin. Upon application, the itching sensations ceased. After several days of applying the solution, "new" skin was observed to be regenerating in the area. This "new" skin was devoid of the previous skin's discoloration and was void of any itching sensations.

Similarly, one of the female subjects applied the solution of the present invention upon a scaly, itchy birthmark located on the mid-thigh area. After a few days of topical application of the solution, the scaly skin was no longer observed and was accompanied by a commensurate elimination of itchiness.

Both female subjects in this example exhibited wrinkled skin in various areas, including the face and chest. These particular wrinkles are also commonly referred to as "smoker's wrinkles" and "stress lines". The solution was applied to these wrinkled areas three times a day. In some cases, the solution may be applied more frequently in order to enhance the appearance of the skin.

Improvements in the appearance of the effected skin were noted after as few as four days of usage. The "stress lines" and wrinkles were visibly reduced. The efficacy of the topically applied solution was such that in one instance, the reduction in observable wrinkles caused the skin to regain a younger overall appearance. As a result, one female subject felt that the application of heavy make-up, which she had previously used to hide-the wrinkles, was superfluous.

EXAMPLE 4

This example demonstrates the effect of the formulations and solutions upon healthy normal skin. Here, the solutions and formulations of the present invention are utilized as part of a normal regimen for the maintenance of normal, healthy skin.

Typically the solution is sprayed onto the users' skin and then rubbed in, with fingertips until dry. The solution may also be applied utilizing various application techniques such as the use of an atomizer, spray bottle and other methods of application of solutions to skin, as known to those skilled in the art. If the solution is to be utilized in the facial area, care must be taken in order not to allow the solution to enter the eyes. If the solution is applied utilizing a spray bottle, for example, the user must close his or her eyes before spraying or misting the solution onto the face. This application can be repeated daily, with the frequency of application being as deemed necessary to achieve the desired effect of healthy, smooth skin.

Recommended use is once a day, unless the need to enhance skin appearance demands more frequent application of the solution. The solution is sprayed onto the desired area, a face for example, and rubbed in. As a result of the application of the solution in this manner, smooth healthy skin is maintained.

It should be noted that many other dilutions of the "full-strength" solution can be made and can be advantageously applied to treat skin problems; often a particular dilution of the "full-strength" formulation is determined by testing various concentrations to determine a "best" concentration. All of these alternate dilutions are thus also within the scope and spirit of the present invention. Finally it will be realized that while each of the aforementioned dilutions have been characterized as dilutions of the "full-strength" solution, any could be made directly by mixing together appropriate amounts of SB, SC and TSP in the proper molar ratio of approximately 1:2.6:1.6, respectively.

In some embodiments, it has additionally been found advantageous to formulate the present solution in a particular manner. Thus in some embodiments, the appropriate amount of sodium bicarbonate (SB) is added to deionized, softened or RO water and stirred until dissolved. While SB is known to be quite soluble in water, it has been found to be advantageous to add the SB to water that has been warmed to between 30 to 40, preferably about 32 degrees Celsius (° C.) to hasten dissolution. Once the SB is dissolved, the appropriate amount of sodium carbonate (SC) is added to the SB solution, again with stirring. Upon addition of the SC, it will be noted that a hazy solution is obtained, and even after prolonged stirring, the solution does not become fully clear. Finally the appropriate amount of trisodium phosphate (TSP) is added to the mixture of SB and SC, again with stirring. It will be noted that after addition of the TSP, in a short time (a few minutes) the mixture becomes clear, denoting a true solution of the three components.

One of ordinary skill in the art will realize that other methods of making the solution can be used. For example, the SC can be added to the water as the first step in preparing the solution. In addition, it is possible to use any one or several of the various hydrated forms of the several components rather than the anhydrous materials specified above. As known, where such hydrated forms are employed, the amount of hydrated material is adjusted to provide the appropriate "anhydrous equivalent weight" to obtain the appropriate molar ratio of approximately 1:2.6:1.6. However, these other methods of making the solution are within the scope and spirit of the present disclosure.

In some embodiments, the solution is formulated to be sprayed onto the affected area using a conventional sprayer. After the solution has been sprayed onto the affected area, it may be rubbed into the skin or tissue with fingers until dry. An applicator, cotton ball, etc is not advised, as it might absorb the solution.

In addition to its action to suppress the growth of microorganisms such as fungus, the solution also exhibits activity against a wide variety of other microorganisms. For example, certain embodiments contemplate application to tissue surfaces to act as a antibacterial solution, eliminating some viable bacteria on contact, and essentially all the remaining bacteria upon drying as a film or thin coating. This result is believed to be due, at least in part, from the encapsulating properties of the film or coating that is formed on drying. In some embodiments, a second application of the solution is made to the tissue surface and allowed to dry, as described above. It has been found that where such a second application is made, the inhibition of re-growth of microorganisms, for example, bacteria and fungi, on the treated surface is extended. The film or coating formed upon drying is a hard, lubricious coating that has been found to be between approximately 2 to 10 microns thick. It is believed that the active agents, within the solution, combine to form an encapsulant that prevents the growth of microorganisms.

It should be apparent that a general-purpose antibacterial and antiseptic solution has been described that encompasses only three common, readily available components. It should also be apparent that the present solution can be formulated in a variety of concentrations so as to be able to provide antibacterial, anti-fungal, and antiseptic properties. In addition, it should be apparent that as each of the components of the solution are safe and essentially non-toxic material (even when taken internally), the mixture of these three components is also safe and essentially non-toxic.

Additionally, it should be apparent that the present solution has sequestering properties that enable it to be applied to a wide variety of skin and tissue problems. It should also be apparent that embodiments possess anti-fungal and anti-bacterial properties that extend by and through the formation of the thin film on drying.

What is claimed is:

1. A method of reducing or eliminating microorganisms on mammalian tissue comprising the acts of:

topically applying a solution consisting essentially of sodium bicarbonate, sodium carbonate and trisodium phosphate having a molar ratio of approximately 1:2.6:1.6, to a surface of the mammalian tissue; and allowing the applied solution to dry wherein a film is formed thereof, thereby to reduce or eliminate the microorganisms from said surface of the tissue.

2. The method of claim 1, wherein said surface of the tissue is a skin surface having a sore, irritation, or scratch.

3. The method of claim 1, further comprising allowing said film to remain on said surface, thereby continuing to reduce or eliminate microorganisms underneath the film.

4. The method of claim 1, wherein said surface is a skin surface having acne, whereby the film blocks microorganisms from entering an infected skin follicle.

5. The method of claim 1, wherein the act of topically applying includes spraying.

6. The method of claim 1, further comprising the act of rubbing said solution into said surface of the tissue.

7. A method of reducing or eliminating fungal growth on mammalian tissue comprising the acts of:

topically applying a solution consisting essentially of sodium bicarbonate, sodium carbonate and trisodium phosphate having a molar ratio of approximately 1:2.6:1.6, to the surface of the tissue; and allowing the applied solution to dry wherein a film is formed thereby to encapsulate the fungus.

8. The method of claim 7 wherein said tissue is fingernails or toenails, wherein the fingernails or toenails have the fungal growth.

9. The method of claim 7, wherein the act of topically applying includes spraying.

10. The method of claim 7, further comprising the act of rubbing said solution into said tissue.

11. A method for promoting healing of mammalian skin, comprising the acts of:

applying to a surface of the skin a therapeutically effective solution, wherein said solution consists essentially of sodium bicarbonate, sodium carbonate and trisodium phosphate having a molar ratio of approximately 1:2.6:1.6; and allowing the applied solution to dry wherein a film is formed on the surface of the skin.

12. The method of claim 11, further comprising applying said solution repeatedly to said surface to promote healing.

13. The method of claim 11 wherein said surface has a sore, irritation, or scratch.

14. The method of claim 11, wherein the act of topically applying includes spraying.

15. The method of claim 11 wherein said skin has a disorder selected from the group consisting of psoriasis, eczema, acne, dermatitis, aging skin, and age spots.

16. A method of promoting skin healing and maintenance comprising the steps of:

applying to skin a therapeutically effective aqueous solution, said solution consisting essentially of sodium bicarbonate, sodium carbonate and trisodium phosphate having a molar ratio of approximately 1:2.6:1.6; and allowing the applied solution to dry wherein a film is formed on the surface of the skin.

17. The method of claim 16, further comprising applying said solution repeatedly to said skin to promote healing.

18. The method of claim 16, wherein said skin has a disorder selected from the group consisting of scars, rashes, burns, stress lines and wrinkles.

19. The method of claim 16, wherein said solution is applied to skin in order to hinder degradation of said skin.

20. The method of claim 16, wherein the application of said solution includes spraying.

21. The method of claim 16, wherein said aqueous portion of said solution is deionized water.

22. The method of claim 16, wherein said aqueous portion of said solution is softened water.

23. The method of claim 16, wherein said aqueous portion of said solution is water which has been processed through a reverse osmosis system.

24. The method of claim 16, wherein the sodium portion of said bicarbonate, carbonate and phosphate compounds may be substituted with other Group IA alkali metals selected from the group consisting of hydrogen, lithium, potassium, rubidium, and cesium.

25. The method of claim 16, wherein said therapeutically effective aqueous solution is comprised of a combination of alkali bicarbonate, alkali carbonate and tri-alkali phosphate compounds having a molar ratio of approximately 1:2.6:1.6, wherein said alkali portions of said compounds are selected from the Group IA alkali metals consisting of hydrogen, lithium, potassium, rubidium, and cesium.

26. The method of claim 16, wherein said solution is aqueous.

* * * * *